(12) United States Patent
Fankhauser

(10) Patent No.: US 8,313,736 B2
(45) Date of Patent: Nov. 20, 2012

(54) CHEMICALLY STABLE INGREDIENTS AS LEMON ODORANT

(75) Inventor: Peter Fankhauser, Meyrin (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/060,498

(22) PCT Filed: Oct. 9, 2009

(86) PCT No.: PCT/IB2009/054443
§ 371 (c)(1),
(2), (4) Date: Feb. 24, 2011

(87) PCT Pub. No.: WO2010/044031
PCT Pub. Date: Apr. 22, 2010

(65) Prior Publication Data
US 2012/0003170 A1    Jan. 5, 2012

(30) Foreign Application Priority Data
Oct. 13, 2008   (EP) .................................... 08166478

(51) Int. Cl.
*A61Q 15/00* (2006.01)
*A61Q 5/02* (2006.01)
*A61Q 19/10* (2006.01)
*A61Q 13/00* (2006.01)
*A61L 9/01* (2006.01)
*A61K 8/40* (2006.01)

(52) U.S. Cl. ............... 424/65; 510/101; 512/6; 514/788
(58) Field of Classification Search .................... 424/65; 558/462; 512/6; 510/101; 514/788
See application file for complete search history.

(56) References Cited

U.S. PATENT DOCUMENTS

| 3,655,722 A | 4/1972 | Mitchell et al. ............ 260/465.9 |
| 3,960,923 A | 6/1976 | DeSimone ................ 260/465.9 |

OTHER PUBLICATIONS

International Search Report and Written Opinion, application No. PCT/IB2009/054443, mailed Jan. 18, 2010.
I.K. Sarycheva et al., Zhurnal Obshchei Khimii, 29:1189-1192 (1959). English translation not available.

*Primary Examiner* — Kristin Bianchi
(74) *Attorney, Agent, or Firm* — Winston & Strawn LLP

(57) ABSTRACT

The present invention discloses certain nitrile compounds that are chemically stable and are useful as a lemon odorant or to impart a lemon odor to various consumer articles. The invention also relates to the compositions and articles that contain such compounds as well to the use of the compounds in a method of imparting a lemon odor to the compositions and articles.

16 Claims, No Drawings

CHEMICALLY STABLE INGREDIENTS AS LEMON ODORANT

This application is a 371 filing of International Patent Application PCT/IB2009/054443, filed Oct. 9, 2009.

TECHNICAL FIELD

The present invention relates to the field of perfumery. More particularly, it concerns some specific nitrile derivatives, very useful for conferring lemon type odor notes. The present invention concerns the use of said compounds in the perfumery industry as well as the compositions or articles containing said compounds.

PRIOR ART

Citral, and related derivatives (such as citronellal, citronellol, geraniol, etc. . . . ), are natural compounds which are in part responsible for the typical and natural citrus/lemon notes and tonalities in citrus fruits. However, these compounds are not stable and are chemically degraded very easily, especially in basic or oxidizing medium. So their use is limited.

Consequently, one long-lasting need of the perfumery industry is the finding of citrus odorant, which possesses an odor as close as possible to those of the natural compounds, which are stable on various applications' medium, such as bleaching.

Although not ideal from a perfumistic point of view (too nitrile), until recently, the almost universally compound used as replacer of citral and similar was geranyl nitrile (3,7-dimethyl-2,6-octadienenitrile). However, recently geranyl nitrile has been banned because mutagenic.

Recently, the industry started to use 3,7-dimethyl-2,6-nonadienenitrile (lemonile) as ingredient to replace geranyl nitrile or citral. However, this compound is not as good as geranyl nitrile, not to mention citral itself.

Therefore, the perfumer's palette has still a need for compounds having a citrus character stronger and/or more developed than the prior art nitrile, and of course if possible being more environmentally friendly. It is an aim of the present invention to solve this problem by providing ingredients which are chemically more stable, organoleptically as close as possible to citral and its natural derivatives (or at least closer than the prior art nitrile), and/or being acceptable for the environment/organisms.

To the best of our knowledge, amongst the invention's compounds, only 3,6,7-trimethyl-2,6-octadienenitrile (with no stereochemistry) is mentioned in a document (see I. K. Sarycheva et al. in Zhurnal Obshchei Khimii, 1959, 29, 1189). In said document, the compound of the invention is mentioned as a chemical intermediate in a synthesis. However, this prior art document does not report or suggest any organoleptic properties of the compounds of formula (I), or any use of said compounds in the field of perfumery.

SUMMARY OF THE INVENTION

The present invention discloses certain nitrile compounds that are chemically stable and are useful to impart a lemon odor to various consumer articles. These compounds can be used by themselves or in perfuming compositions. The invention also relates to a method of imparting a lemon odor to such compositions and articles through the use of such compounds.

DESCRIPTION OF THE INVENTION

We have now surprisingly discovered that a compound of formula

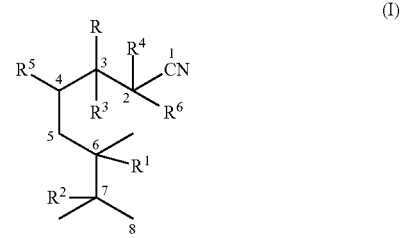

(I)

wherein R represents a methyl or ethyl group;

$R^6$ represents a hydrogen atom or a methyl or ethyl group;

$R^1$ and $R^2$, taken separately, represent each a hydrogen atom or a $OR^7$ group, $R^7$ being a hydrogen atom or a $C_{1-2}$ alkyl or acyl group; or said $R^1$ and $R^2$, taken together, represent an oxygen atom, a $CH_2$ group or a carbon-carbon double bond; and $R^3$, $R^4$ and $R^5$ are each a hydrogen atom; or a) $R^5$ is a hydrogen atom and $R^3$ and $R^4$, taken together, represent an oxygen atom, a $CH_2$ group or a carbon-carbon double bond; or b) $R^4$ is a hydrogen atom and $R^3$ and $R^5$, taken together, represent an oxygen atom, a $CH_2$ group or a carbon-carbon double bond;

can be used as perfuming ingredient, for instance to impart odor notes of the lemon type.

For the sake of clarity, by the expression "$R^3$ and $R^4$, taken together, represent . . . a carbon-carbon double bond", or the similar, it is meant the normal meaning understood by a person skilled in the art, i.e. that the whole bonding between the carbon atoms bearing said R groups, e.g. carbon 2 and 3, is a carbon-carbon double bond.

According to a particular embodiment of the invention, said compound (I) is a $C_{11}$-$C_{13}$ or even a $C_{11}$-$C_{12}$ compound, and in particular those wherein one or two carbon-carbon double bonds are present.

The compounds (I) wherein R is a methyl group represent a specific embodiment of the invention.

The compounds (I) wherein $R^6$ is a hydrogen atom or a methyl group, represent a specific embodiment of the invention, in particular when $R^6$ is a hydrogen atom.

According to a particular embodiment of the invention, said compounds (I) are of formula (I), wherein R represents a methyl or ethyl group;

$R^6$ represents a hydrogen atom or a methyl group;

$R^1$ and $R^2$, taken separately, represent each a hydrogen atom or said $R^1$ and $R^2$, taken together, represent a $CH_2$ group or a carbon-carbon double bond; and $R^3$, $R^4$ and $R^5$ are each a hydrogen atom; or a) $R^5$ is a hydrogen atom and $R^3$ and $R^4$, taken together, represent a $CH_2$ group or a carbon-carbon double bond; or b) $R^4$ is a hydrogen atom and $R^3$ and $R^5$, taken together, represent a $CH_2$ group or a carbon-carbon double bond.

According to a particular embodiment of the invention, said compounds (I) are of formula

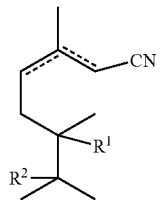

(II)

wherein one dotted line represents a carbon-carbon single bond and the other a carbon-carbon single or double bond; $R^1$ and $R^2$, taken separately, represent a hydrogen atom or a $OR^7$ group, $R^7$ being a hydrogen atom or a methyl, ethyl or acetyl group, or said $R^1$ and $R^2$, taken together, represent a oxygen atom, a carbon-carbon double bond or a $CH_2$ group.

According to a particular embodiment of the invention, said compounds (I) are of formula (II), wherein
one dotted line represents a carbon-carbon single bond and the other a carbon-carbon single or double bond;
$R^1$ and $R^2$, taken separately, represent a hydrogen atom or said $R^1$ and $R^2$, taken together, represent a carbon-carbon double bond or a $CH_2$ group.

According to a further embodiment of the present invention, said compounds (I) are of formula

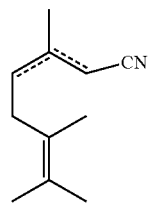

(III)

wherein one dotted line represents a carbon-carbon single bond and the other a carbon-carbon single or double bond.

In particular, for the compounds (II) or (III) of the above embodiments, the dotted line between positions 3 and 4 is a single bond.

For the sake of clarity, by the expression "wherein one dotted line represents a carbon-carbon single bond and the other a carbon-carbon single or double bond", or the similar, it is meant the normal meaning understood by a person skilled in the art, i.e. that the whole bonding (solid and dotted line) between the carbon atoms connected by said dotted line, e.g. carbons 2 and 3, is a carbon-carbon single or double bond.

As can be foreseen from formula (I), some of the invention's compounds can be in an optically active form, or for some of the invention's compounds the carbon-carbon double bond next to the nitrile group, when present, can be in a configuration E or Z or a mixture thereof. Therefore, it is clear that the invention's compound can be in the form of any one of its optical or configuration isomers or of a mixture thereof. In particular the compound (III) can be in the form of a mixture of E and Z isomers. According to a particular embodiment, said compound (I), (II) or (III) can be in the form of a mixture of E and Z isomers wherein the E isomer represents at least 75% w/w (or a E/Z ratio of at least 3).

The compounds of formula (I), as well as (II) or (III), distinguish from the prior art perfuming ingredient of similar structure by having an additional methyl group on position 6 of the main chain. These compounds are all new, at the exception of 3,6,7-trimethyl-2,6-octadienenitrile as mentioned above, and therefore are also an object of the present invention.

As specific, but non-limiting, examples of the invention's compounds one may cite the following ones in Table 1:

TABLE 1

Invention's compounds and their odor properties

| Compound structure and name | Odour and comparison with known ingredients |
|---|---|
| 3,6,7-trimethyl-2,6-octadienenitrile | Very nice and natural lemon, lemon peel note. Close to the one of geranyl nitrile, but much less fatty and more lemony than the latter. Olfactively much closer to citral than to geranyl nitrile. Less chemical and more zest/peel and natural than lemonile. Compared to citronellyl nitrile, the present compound is by far more lemony, elegant and less fatty. |
| (2E)-3,6,7-trimethyl-2,6-octadienenitrile | Very nice and natural lemony note. The E isomer possesses a stronger lemony character than the above E/Z mixture. |
| (2Z)-3,6,7-trimethyl-2,6-octadienenitrile | Lemony note with a fatty and cumin aspect. The Z isomer possesses a weaker lemony character than the above E/Z mixture. Said compound is olfactively between geranyl nitrile and citral but, although being more citral, closer to geranyl nitrile. |
| 3,6,7-trimethyl-6-octenenitrile | Although structurally close to citronellyl nitrile, this compound is more powerful, elegant, lemony and zest than citronellyl nitrile. |
| (3E)-3,6,7-trimethyl-3,6-octadienenitrile | Lime, citronellol, geranyl nitrile but less aggressive/chemical and less nitrile than the latter. Also some floral/rosy aspects. |
| 3,6,7-trimethyloctanenitrile | Citrus/citral, nitrile, the citral note is stronger than the one of the prior art analogue 3,7-dimethyloctanenitrile. The odor of this invention's compound is close to the one of geranyl nitrile. |

TABLE 1-continued

Invention's compounds and their odor properties

| Compound structure and name | Odour and comparison with known ingredients |
|---|---|
| 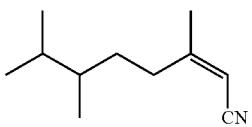<br>(2Z)-3,6,7-trimethyl-2-octenenitrile | Citrus, lemony, green and nitrile, as overall the odor is less fatty/nitrile and more elegant than the one of its analogue 3,7-dimethyl-2-octenenitrile. |
| 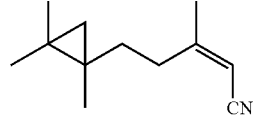<br>3-methyl-5-(1,2,2-trimethylcyclopropyl)-2-pentenenitrile | Citrus, lemony, fruity, nitrile, more natural and less fatty than geranyl nitrile. The citral character of this compound is stronger than the one of geranyl nitrile but is slightly inferior to the one of 3,6,7-trimethyl-2,6-octadienenitrile. |
| 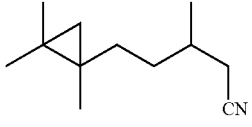<br>3-methyl-5-(1,2,2-trimethylcyclopropyl)pentanenitrile | Nice citrus note, slightly nitrile but well lemony, more citral than the above cyclopropane derivative. Nice and pleasant, more natural than geranyl nitrile. |

As can be seen, the citrus/lemon tonalities of the invention's compounds may vary according to the exact structure of the invention's compounds, exactly as for the citral and its similar derivatives present in the nature. However all the invention's compounds possess a more natural and/or stronger citrus note than the prior art analogues which are not substituted in the 6 position.

According to a particular embodiment of the invention, the compounds of formula (I) are 3,6,7-trimethyl-2,6-octadienenitrile, (2E)-3,6,7-trimethyl-2,6-octadienenitrile and/or 3,6,7-trimethyl-6-octenenitrile.

The organoleptic properties of the invention's compounds are very surprising in view of the prior art. Indeed, on one hand, for citral, and its naturally occurring derivatives, it was known that replacing the heteroatom functional group (CHO or $CH_2OH$) with a nitrile group, although it allows to maintain a lemony character (albeit weaker), it also increases significantly the fatty notes (see citral vs geranyl nitrile, or citronellol vs citronellol nitrile). On the other hand, as 3,6,7-trimethyl-2,6-octadienal (see Arctander 1956) has been described as "not nearly as lemony as citral" (i.e. much less lemony), one would have expected the present compounds (bearing a nitrile group) to have a very weak lemony character (at least weaker than the corresponding prior art nitrile), contrary to the present invention.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any compositions containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Geliermittel in Lebensmittel, Band 2 der Schriftenreihe Lebensmittelchemie, Lebensmittelqualitat, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. . . . . A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords or perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:
i) as perfuming ingredient, at least one compound of formula (I), as defined above, or an invention's perfuming composition; and
ii) a consumer product base;
is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric softeners, fabric refreshers, ironing waters, papers, wipes or bleaches.

According to a particular embodiment of the invention, the consumer products associated with the functional perfumery (e.g. soaps, detergents, deodorant, etc. . . . ) are particularly relevant.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.1% to 15% by weight, or even more, of the compounds of the invention based on the weight of the composition into which they are incorporated. Concentrations lower than these, such as in the order of 0.01% to 5% by weight, can be used when these compounds are incorporated into perfumed articles, percentage being relative to the weight of the article.

As mentioned above, the present compounds are preferably more environmentally friendly than the prior art nitrile. For instance we have unexpectedly found that 3,6,7-trimethyl-2,6-octadienenitrile, in the form of E and Z isomers or of a mixture thereof, is not clastogenic (i.e. does not induce chromosome-damages), to the contrary of the prior art 3,7-dimethyl-2,6-octadienenitrile.

The invention's compounds can be prepared according to a method as described in the examples.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

a) Preparation of 3,6,7-trimethyl-2,6-octadienenitrile and its stereoisomer isomers E or Z and of 3,6,7-trimethyl-3,6-octadienenitrile 5,6-Dimethylhept-5-en-2-one (100 g; 0.707 mol), cyanoacetic acid (81 g; 0.948 mol), triethanolamine (7.8 g; 0.052 mol) and toluene (140 g) were charged in a multi-necked 1 l round bottom flask and heated to reflux. The water formed by the reaction was removed using a dean stark trap. After 21 hours the reaction mixture was cooled to room temperature and washed repeatedly with brine. Drying over anhydrous sodium sulphate, filtration and removal of the solvent afforded the crude nitrile. A distillation through a 15 cm Vigreux column gave 68.5 g of 88% pure methyl geranyl nitrile (mixture of isomers) in a yield of 52% (bp. 61° C. (1 mbar)). Distillation of this product through a 35 cm Fischer Spaltrohr® column allowed to separate the various isomers.

(2Z)-3,6,7-Trimethyl-2,6-octadienenitrile $^{13}$C-NMR: 18.4 (q), 20.2 (q), 20.6 (q), 23.1 (q), 32.8 (t), 35.0 (t), 95.6 (d), 116.9 (s), 125.8 (s), 126.0 (s), 165.5 (s).
$^{1}$H-NMR: 1.65 (s, 3H); 1.68 (s, 6H); 1.93 (s, 3H); 2.20-2.24 (m, 2H); 2.41-2.45 (m, 2H); 5.09 (s, 1H).

(2E)-3,6,7-Trimethyl-2,6-octadienenitrile $^{13}$C-NMR: 18.2 (q), 20.1 (q), 20.6 (q), 21.1 (q), 32.4 (t), 37.2 (t), 95.1 (d), 117.3 (s), 125.6 (s), 125.8 (s), 165.4 (s).
$^{1}$H-NMR: 1.63-1.64 (3s, 9H); 2.07 (s, 3H); 2.19-2.20 (m, 4H); 5.10 (s, 1H).

(3E)-3,6,7-Trimethyl-3,6-octadienenitrile $^{13}$C NMR: 16.0 (q), 18.4 (q), 20.2 (q), 20.6 (q), 27.3 (t), 33.2 (t), 117.9 (s), 124.0 (s). 125.1 (s), 125.6 (s), 128.3 (d).
$^{1}$H-NMR: 1.61 (s, 3H); 1.65 (s, 3H); 1.66 (s, 3H); 1.78 (s, 3H); 2.77 (d, J=7.3, 2H); 3.03 (s, 3H); 5.39-5.43 (m, 2H).

A quality of 3,6,7-trimethyl-2,6-octadienenitrile consisting of a mixture of isomers (2E) and (2Z) wherein the E isomer represents about 85% w/w was obtained by admixing the required amount of the pure E and Z isomers. Said quality was used in the perfumery examples.

b) Preparation of 3,6,7-trimethyl-6-octenenitrile

Methyl citronellal (25.65 g; 0.147 mol) was charged in a multi-necked 100 ml round bottom flask and heated under stirring to 55° C. Hydroxylamine (11.2 g; 0.17 mol, as a 50% aqueous solution) was added dropwise over 20 minutes under stirring and cooling. Stirring was continued at 55° C. for 1 hour, then 0.5 g of sodium acetate was added. After 15 minutes of stirring the reaction mixture was cooled to room temperature and extracted with MTBE (100 ml). the aqueous phase was discarded and the organic phase washed with brine. Drying on anhydrous sodium sulphate, filtration and removal of the solvent afforded the crude oxime as a mixture of two isomers (35.6%, 62.1%).

Sodium acetate (0.6 g; 0.007 mol) and n-heptane (25 ml) were charged in a multi-necked 250 ml round bottom flask and heated under stirring to 100° C. (reflux). The crude oxime (26.5 g; 0.14 mol) and acetic anhydride (17.5 g; 0.17 mol) were added dropwise and simultaneously over 30 minutes under stirring. Stirring was continued at reflux for 30 minutes. The reaction mixture was cooled to room temperature and poured onto ice (100 g), the aqueous phase was discarded and the organic phase washed with aqueous NaHCO$_3$, and brine. Drying on anhydrous sodium sulphate, filtration and removal of the solvent afforded the crude nitrile. A distillation through a 15 cm Vigreux column gave 18.33 g of 97.5% pure desired product in a yield of 79.4% (bp. 67° C. (1 mbar)).

$^{13}$C NMR: 18.3 (q), 19.5 (q), 20.1 (q), 20.6 (q), 24.5 (t), 30.5 (d), 31.7 (t), 34.3 (t), 118.8 (s), 124.6 (s), 126.8 (s);
$^{1}$H-NMR: 1.08-1.10 (d, J=6.64, 6H); 1.30-1.39 (m, 1H); 1.44-1.53 (m, 1H); 1.63 (s, 6H); 1.65 (s, 3H); 1.76-1387 (m, 1H); 1.98-2.09 (m, 2H); 2.23-2.36 (m, 2H).

c) Preparation of 3,6,7-trimethyloctanenitrile 3,6,7-Trimethyl-2,6-octadienenitrile (15 g; 0.092 mol), palladium on charcoal (5% Pd/C, 1.5 g) and ethyl acetate (60 ml) were charged in a 500 ml stirred autoclave and hydrogenated (4 bar hydrogen) at 25° C. for 24 hours. Filtration over celite and removal of the solvent afforded 15.1 g of the saturated nitrile as a mixture of two isomers. Distillation using a 10 cm Vigreux column gave 13.8 g of 98.2% pure 3,6,7-trimethyloctanenitrile (mixture of isomers; 56/42) in a yield of 88%.

Bp. 71° C. (2 mbar).
$^{13}$C NMR major isomer: 15.3 (q), 18.0 (q), 19.4 (q), 20.2 (q), 24.7 (t), 30.9 (d), 31.2 (t), 32.0 (d), 33.8 (t), 38.6 (d), 118.9 (s);
$^{1}$H-NMR: 0.81 (d, J=6.7 Hz, 3H); 0.86 (d, J=6.7 Hz, 3H); 1.06-1.10 (2d, 6H); 1.20-1.35 (m, 7H), 2.21-2.36 (m, 2H).

d) Preparation of (2Z)-3,6,7-trimethyl-2/3-octenenitrile 5,6-Dimethylheptane-2-one, obtained by hydrogenation of 5,6-dimethylhept-5-en-2-one (Pd/C, H$_2$, neat, 20° C.) was converted to the target nitrile using the Knoevenagel reaction conditions described above. Distillation through a 35 cm Fischer Spaltrohr® column allowed to isolate the separate isomers.

(2Z)-3,6,7-trimethyl-2-octenenitrile $^{13}$C-NMR: 15.2 (q), 17.9 (q), 20.2 (q), 22.8 (q), 31.9 (d), 32.1 (t), 34.4 (t), 38.3 (d), 95.4 (d), 117.0 (s), 166.2 (s);
$^{1}$H-NMR: 0.82 (d, J=6.5 Hz, 3H); 0.87 (d, J=6.7 Hz, 3H); 0.88 (d, J=6.8 Hz, 3H); 1.23-1.35 (m, 2H); 1.49-1.56 (m, 1H); 1.57-1.64 (m, 1H); 1.90 (s, 3H); 2.39 (t, 2H); 5.09 (d, J=0.9 Hz, 1H).

(2E)-3,6,7-trimethyl-2-octenenitrile $^{13}$C-NMR: 15.2 (q), 17.9 (q), 20.1 (q), 21.0 (q), 31.5 (t), 31.9 (d), 36.7 (t), 38.1 (d), 94.9 (d), 117.3 (s), 165.9 (s);
$^{1}$H-NMR: 0.81 (d, J=6.7 Hz, 3H); 0.82 (d, J=6.7 Hz, 3H); 0.88 (d, J=6.8 Hz, 3H); 1.19-1.33 (m, 2H); 1.46-1.53 (m, 1H); 1.53-1.61 (m, 1H); 2.05 (d, J=0.9 Hz, 3H); 2.18 (t, 2H); 5.12 (d, J=0.9 Hz, 1H).

(2E)-3,6,7-trimethyl-3-octenenitrile $^{13}$C NMR: 15.4 (q), 16.1 (q), 18.1 (q), 20.3 (q), 27.3 (t), 31.8 (d), 32.6 (t), 39.1 (d), 117.9 (s), 124.4 (s), 129.4 (d);
$^{1}$H-NMR: 0.78-0.89 (3d, 9H); 1.33-1.42 (m, 1H); 1.52-1.62 (m, 1H); 1.73 (s, 3H); 1.82-1.90 (m, 1H); 2.04-2.10 (m, 1H); 3.5 (s, 3H); 5.47-5.51 (m, 1H).

e) Preparation of 3-methyl-5-(1,2,2-trimethylcyclopropyl)-2-pentenenitrile

To an oven dried 2000 ml round bottomed flask was added methylene chloride (700 ml) under a nitrogen atmosphere. Diethylzinc (350 ml, 1 m in hexanes; 0.350 mol) was added, and then diiodomethane (184.5 g, 0.69 mol) was introduced dropwise over 1.5 hour. following stirring for 1 hour (a white precipitate formed) 3,6,7-trimethyl-2,6-octadienenitrile (14 g, 0.086 mol; 15/85 Z/E mixture) was added dropwise over 30 minutes and the reaction was stirred for 45 hours at room temperature. The reaction mixture was poured into a 20% aqueous potassium carbonate solution (750 ml) and then filtered through a pad of celite in a sintered funnel. The organic layer was separated and dried over anhydrous sodium sulfate. Filtration of the drying agent, concentration and flash distillation gave 41.4 g of crude material. This product, containing 35% of starting nitrile was subjected to a second cyclopropanation procedure. Distillation through a Vigreux column followed by flash chromatography (silica; eluant=heptanes/ mtbe) gave the title compound as a Z/E isomer mixture.

B.P.=55° c. (1 mbar).

$^{13}$C NMR: 19.3 (q), 20.1 (s), 21.2 (q), 22.3 (q), 22.6 (q), 23.0 (s), 27.0 (t), 34.6 (t), 36.7 (t), 94.7 (d), 117.3 (s), 166.0 (s).

$^{1}$H-NMR: 0.12-0.16 (m, 2H); 1.07-1.10 (3s, 9H); 1.36-1.62 (m, 2H); 2.05 (d, J=1.0 Hz, 3H); 2.16-2.32 (m, 2H); 5.09-5.10 (m, 1H).

f) Preparation of 3-methyl-5-(1,2,2-trimethylcyclopropyl)pentanenitrile

The title compound was prepared by cyclopropanation of methyl citronellyl nitrile. A procedure analogous to the one above was used. The title compound was obtained as a diastereomeric mixture.

$^{13}$C NMR: 19.5 (q), 19.6 (q), 19.9 (s), 22.3 (q), 22.7 (q), 23.2 (s), 24.6 (t), 27.1 (t), 31.0 (d), 33.5 (t), 34.0 (t), 118.9 (s);

$^{1}$H-NMR: 0.09-0.12 (m, 2H); 1.05-1.10 (3s, 9H); 1.09-1.10 (d, J=2.6 Hz, 3H); 1.20-1.67 (m, 4H); 1.76-1.84 (m, 1H); 2.21-2.35 (m, 2H).

Example 2

Preparation of a Perfuming Composition

A perfuming composition of the lemon type for an "all purpose cleaner" was prepared by admixing the following ingredients:

| Ingredient | Parts by weight |
| --- | --- |
| Isobornyl acetate | 60 |
| Citronellyl acetate | 40 |
| Geranyl acetate | 90 |
| Linalyl acetate | 150 |
| Myrcenyl acetate | 40 |
| C 10 Aldehyde | 50 |
| C 8 Aldehyde | 50 |
| C 9 Aldehyde | 20 |
| Hexylcinnamic aldehyde | 110 |
| MNA aldehyde | 20 |
| Citronellol | 70 |
| Dihydromyrcenol | 80 |
| Florol ® [1] | 10 |
| Geraniol | 120 |
| Linalool | 110 |
| 10% * Methyl naphtyl ketone | 30 |
| Hedione ® [2] | 80 |
| Rose oxide | 15 |
| Paracymene | 80 |
| Pinenes | 35 |
| Turpentine | 100 |
| Orange terpenes | 850 |
| Terpineol | 100 |
| Terpinolene | 100 |
| 1,4/8-Epoxy-p-menthane | 80 |
| 2,4-Dimethyl-3-cyclohexene-1-carbaldehyde | 10 |
| | 2500 |

* in dipropyleneglycol
[1] tetrahydro-2-isobutyl-4-methyl-4(2H)-pyranol; origin: Firmenich SA, Geneva, Switzerland
[2] methyl dihydro jasmonate; origin: Firmenich SA, Geneva, Switzerland The addition of 250 parts by weight of 3,6,7-trimethyl-2,6-octadienenitrile imparted to the original composition a lemon character and a functional aspect, which are absolutely mandatory for this type of home care products.

The addition of 3,6,7-trimethyl-2,6-octadienenitrile provided an overall effect as good as, and even more lemony than, the addition of the same amount of geranyl nitrile (which was the universally used ingredient for this kind of consumer products but cannot be used any more in perfumery).

When to the original composition were added the same amount of citronellyl nitrile (a replacement of geranyl nitrile) the overall effect was disappointing, flat, fatty, much less lemony!

When to the original composition were added the same amount of lemonile (another replacement of geranyl nitrile) the overall effect was almost as lemony as the one obtained with 3,6,7-trimethyl-2,6-octadienenitrile, but more disharmonious, less natural and more chemical.

When to the original composition were added the same amount of 3,6,7-trimethyl-6-octenenitrile, the overall effect was much more lemony, powerful, elegant and natural than the one obtained with citronellyl nitrile.

Example 3

Preparation of a Perfuming Composition

A perfuming composition of the "citrus, herbaceous" type for a shower gel was prepared by admixing the following ingredients:

| Ingredient | Parts by weight |
| --- | --- |
| Benzyl acetate | 100 |
| Styrallyl acetate | 30 |
| Terpenyl acetate | 100 |
| C 10 Aldehyde | 10 |
| 50% * C 12 Aldehyde | 20 |
| 10% * C 8 Aldehyde | 20 |
| Hexylcinnamic Aldehyde | 210 |
| Allyl Amyl Glycolate | 20 |
| 10% * Calone ® [1] | 30 |
| Cetalox ® [2] | 10 |
| 10%* Cis-3-Hexenol | 50 |
| Lemon essential oil | 100 |
| Citronellol | 70 |
| Citronnelle | 20 |
| 10% * Damascone Alpha | 40 |
| Dihydromyrcenol | 450 |
| Estragon | 10 |
| Ethyl amyl ketone | 10 |
| Diethyl 1,4-cyclohexane dicarboxylate [3] | 30 |
| Geraniol | 60 |
| Hedione ® [4] | 250 |
| Helvetolide ® [5] | 100 |
| Iralia ® Total [6] | 50 |
| 10% * Isobutylquinoleine | 20 |
| Lavandin Grosso | 80 |
| Lilial ® [7] | 250 |
| *Litsea Cubeba* essential oil | 60 |
| Mandarine essential oil | 40 |
| Mint essential oill | 10 |
| 10% * Menthone | 40 |
| Muscenone [8] Delta | 50 |
| 10% * Neobutenone ® Alpha [9] | 20 |
| Nirvanol ® [10] | 40 |
| 10% * Cis-2-methyl-4-propyl-1,3-oxathiane | 20 |
| Rose oxyde | 10 |
| *Patchouli* essential oil | 30 |
| Orange essential oil | 100 |
| Benzyl salicylate | 220 |
| Terpinolene | 100 |
| 10% * Vanilline | 40 |

-continued

| Ingredient | Parts by weight |
|---|---|
| Vertofix® [11] Coeur | 70 |
| 2,4-Dimethyl-3-cyclohexene-1-carbaldehyde | 10 |
| | 3000 |

* in dipropyleneglycol
[1] 7-methyl-2H-1,5-benzodioxepin-3(4H)-one; origin: Firmenich SA, Geneva, Switzerland
[2] dodecahydro-3a,6,6,9a-tetramethyl-naphtho[2,1-b]furan; origin: Firmenich SA, Geneva, Switzerland
[3] origin: Firmenich SA, Geneva, Switzerland
[4] methyl dihydro jasmonate; origin: Firmenich SA, Geneva, Switzerland
[5] (1S,1'R)-2-[1-(3',3'-dimethyl-1'-cyclohexyl)ethoxy]-2-methylpropyl propanoate; origin: Firmenich SA, Geneva, Switzerland
[6] mixture of methylionones isomers; origin: Firmenich SA, Geneva, Switzerland
[7] 3-(4-tert-butylphenyl)-2-methylpropanal; origin: Givaudan-Roure SA, Vernier, Switzerland
[8] 3-methyl-(4/5)-cyclopentadecenone; origin: Firmenich SA, Geneva, Switzerland
[9] 1-(5,5-dimethyl-1-cyclohexen-1-yl)-4-penten-1-one; origin: Firmenich SA, Geneva, Switzerland
[10] 3,3-dimethyl-5-(2,2,3-trimethyl-3-cyclopenten-1-yl)-4-penten-2-ol; origin: Firmenich SA, Geneva, Switzerland
[11] methyl cedryl ketone; origin: International Flavors & Fragrances, USA The addition of 100 parts by weight of 3,6,7-trimethyl-2,6-octadienenitrile imparted to the above shower gel a clear lemon/lime connotation.

The addition of the same amount of geranyl nitrile or lemonile did not allow obtaining the same effect. Indeed in the case of geranyl nitrile the new fragrance was too much fatty and rosy like, while in the case of lemonile the new fragrance was too much fatty and citronella like.

Example 4

In vivo testing of toxicity of 3,6,7-trimethyl-2,6-octadienenitrile vs 3,7-dimethyl-2,6-octadienenitrile In vivo test for clastogenic effects performed on 3,6,7-trimethyl-2,6-octadienenitrile and 3,7-dimethyl-2,6-octadienenitrile under the conditions required by the standard test protocol for Mammalian Erythrocyte Micronucleus Test (OECD 474, OECD web site http://lysander.sourceoecd.org/v1=155221/c1=19/nw=1/rpsv/ij/oecdjournals/1607310x/v1n 4/s39/p1) gave the following results:
- 3,6,7-trimethyl-2,6-octadienenitrile: the test was negative (i.e. no perceived toxicity) in the dose range between 200-1200 mg/kg.
- 3,7-dimethyl-2,6-octadienenitrile: the test was positive (i.e. perceived toxicity) in the dose range between 500-1250 mg/kg (overlapping the dose range of the invention compound herein above). This ingredient has been banned for its clastogenic effect.

What is claimed is:

1. A perfuming composition comprising:
   i) at least a compound of formula (I)

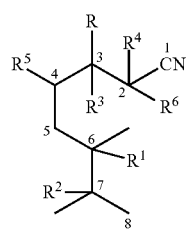

wherein R represents a methyl or ethyl group;
$R^6$ represents a hydrogen atom or a methyl or ethyl group;
$R^1$ and $R^2$, taken separately, represent each a hydrogen atom or a $OR^7$ group, $R^7$ being a hydrogen atom or a $C_{1-2}$ alkyl or acyl group; or $R^1$ and $R^2$, taken together, represent an oxygen atom, a $CH_2$ group or a carbon-carbon double bond; and
$R^3$, $R^4$ and $R^5$ are each a hydrogen atom; or
   a) $R^5$ is a hydrogen atom and $R^3$ and $R^4$, taken together, represent an oxygen atom, a $CH_2$ group or a carbon-carbon double bond; or
   b) $R^4$ is a hydrogen atom and $R^3$ and $R^5$, taken together, represent an oxygen atom, a $CH_2$ group or a carbon-carbon double bond;
   wherein the compound is in the form of any one of its optical or configuration isomers or of a mixture thereof;
ii) at least one ingredient selected from the group consisting of a perfumery carrier and a perfumery base, and
iii) optionally at least one perfumery adjuvant.

2. The perfuming composition according to claim 1, wherein the compound (I) is 3,6,7-trimethyl-2,6-octadienenitrile, (2E)-3,6,7-trimethyl-2,6-octadienenitrile, (2Z)-3,6,7-trimethyl-2,6-octadienenitrile, 3,6,7-trimethyl-6-octenenitrile or (3E)-3,6,7-trimethyl-3,6-octadienenitrile.

3. A perfumed article comprising:
at least one compound of formula (I)

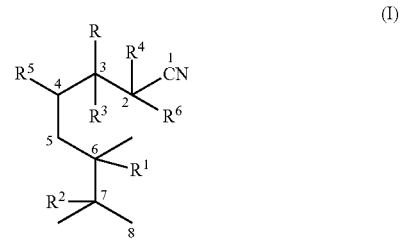

wherein R represents a methyl or ethyl group;
$R^6$ represents a hydrogen atom or a methyl or ethyl group;
$R^1$ and $R^2$, taken separately, represent each a hydrogen atom or a $OR^7$ group, $R^7$ being a hydrogen atom or a $C_{1-2}$ alkyl or acyl group; or $R^1$ and $R^2$, taken together, represent an oxygen atom, a $CH_2$ group or a carbon-carbon double bond; and
$R^3$, $R^4$ and $R^5$ are each a hydrogen atom; or
   a) $R^5$ is a hydrogen atom and $R^3$ and $R^4$, taken together, represent an oxygen atom, a $CH_2$ group or a carbon-carbon double bond; or
   b) $R^4$ is a hydrogen atom and $R^3$ and $R^5$, taken together, represent an oxygen atom, a $CH_2$ group or a carbon-carbon double bond;
   wherein the compound is in the form of any one of its optical or configuration isomers or of a mixture thereof; and
i) a consumer product base.

4. The perfumed article according to claim 3, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

5. A method to confer, enhance, improve or modify the odor properties of a perfuming composition or of a perfumed article, which method comprises adding to the composition or article an effective amount of at least a compound of formula

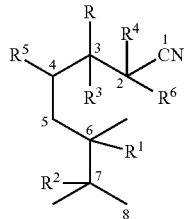

(I)

wherein R represents a methyl or ethyl group;
$R^6$ represents a hydrogen atom or a methyl or ethyl group;
$R^1$ and $R^2$, taken separately, represent each a hydrogen atom or a $OR^7$ group, $R^7$ being a hydrogen atom or a $C_{1-2}$ alkyl or acyl group; or said $R^1$ and $R^2$, taken together, represent an oxygen atom, a $CH_2$ group or a carbon-carbon double bond; and
$R^3$, $R^4$ and $R^5$ are each a hydrogen atom; or
  a) $R^5$ is a hydrogen atom and $R^3$ and $R^4$, taken together, represent an oxygen atom, a $CH_2$ group or a carbon-carbon double bond; or
  b) $R^4$ is a hydrogen atom and $R^3$ and $R^5$, taken together, represent an oxygen atom, a $CH_2$ group or a carbon-carbon double bond;
wherein the compound is in the form of any one of its optical or configuration isomers or of a mixture thereof.

6. The method according to claim 5, wherein the compound of formula (I) is of formula (II):

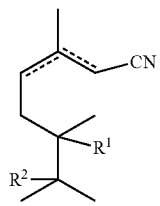

(II)

wherein the dotted lines indicates where an additional carbon-carbon bond is present and only one additional carbon-carbon bond in present in the compound; and
$R^1$ and $R^2$, taken separately, represent a hydrogen atom, or $R^1$ and $R^2$, taken together, represent a carbon-carbon double bond or a $CH_2$ group.

7. The method according to claim 5, wherein the compound of formula (I) is of formula (III):

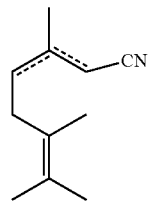

(III)

wherein the dotted lines indicates where an additional carbon-carbon bond is present and only one additional carbon-carbon bond is present in the compound.

8. The method according to claim 5, wherein the compound of formula (I) is 3,6,7-trimethyl-2,6-octadienenitrile, (2E)-3,6,7-trimethyl-2,6-octadienenitrile, (2Z)-3,6,7-trimethyl-2,6-octadienenitrile, 3,6,7-trimethyl-6-octenenitrile or (3E)-3,6,7-trimethyl-3,6-octadienenitrile.

9. The method according to claim 5, wherein the compound of formula (I) is 3,6,7-trimethyl-2,6-octadienenitrile, (2E)-3,6,7-trimethyl-2,6-octadienenitrile, or 3,6,7-trimethyl-6-octenenitrile.

10. The method according to claim 5, wherein the compound of formula (I) is added with at least one ingredient selected from the group consisting of a perfumery carrier and a perfumery base, and optionally at least one perfumery adjuvant.

11. The method according to claim 5, wherein the compound of formula (I) is added to a consumer product base.

12. The method according to claim 11, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

13. A perfuming composition comprising
  i) at least a compound of formula (III):

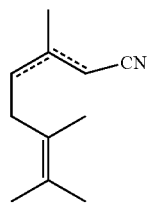

(III)

wherein the dotted lines indicates where an additional carbon-carbon bond is present and only one additional carbon-carbon bond is present in the compound;
  ii) at least one ingredient selected from the group consisting of a perfumery carrier and a perfumery base, and
  iii) optionally at least one perfumery adjuvant.

14. A perfumed article comprising:
  ii) at least one compound of formula (III):

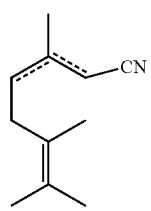

(III)

wherein the dotted lines indicates where an additional carbon-carbon bond is present and only one additional carbon-carbon bond is present in the compound;
  iii) a consumer product base.

15. The perfumed article according to claim 14, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

16. The perfumed article according to claim 3, wherein the compound (I) is 3,6,7-trimethyl-2,6-octadienenitrile, (2E)-3,6,7-trimethyl-2,6-octadienenitrile, (2Z)-3,6,7-trimethyl-2,6-octadienenitrile, 3,6,7-trimethyl-6-octenenitrile or (3E)-3,6,7-trimethyl-3,6-octadienenitrile.

* * * * *